(12) United States Patent
Hsu et al.

(10) Patent No.: US 11,138,558 B2
(45) Date of Patent: Oct. 5, 2021

(54) SYSTEM AND METHOD FOR MANAGING FOOD INFORMATION BASED ON ITS ODOR

(71) Applicant: TAIWAN CARBON NANO TECHNOLOGY CORPORATION, Miaoli County (TW)

(72) Inventors: Ching-Tung Hsu, Miaoli County (TW); Chun-Wei Shih, Miaoli County (TW); Kuang-Che Lee, Miaoli County (TW); Chia-Hung Li, Miaoli County (TW); Chien-Yao Huang, Miaoli County (TW); Chun-Hsien Tsai, Miaoli County (TW); Ting-Chuan Lee, Miaoli County (TW); Chun-Jung Tsai, Miaoli County (TW)

(73) Assignee: TAIWAN CARBON NANO TECHNOLOGY CORPORATION, Zhunan Township (TW)

( * ) Notice: Subject to any disclaimer, the term of this patent is extended or adjusted under 35 U.S.C. 154(b) by 0 days.

(21) Appl. No.: 16/825,484

(22) Filed: Mar. 20, 2020

(65) Prior Publication Data
US 2020/0302379 A1     Sep. 24, 2020

(30) Foreign Application Priority Data

Mar. 22, 2019   (TW) .................................. 108110106

(51) Int. Cl.
*G06Q 10/08*     (2012.01)
*G01N 33/02*     (2006.01)
(Continued)

(52) U.S. Cl.
CPC ........... *G06Q 10/087* (2013.01); *G01N 33/02* (2013.01); *G06K 9/62* (2013.01); *G06K 19/07* (2013.01);
(Continued)

(58) Field of Classification Search
CPC ........ G01N 31/22; G01N 33/02; G06F 21/64; G06K 19/07; G06K 9/62; G06Q 10/06;
(Continued)

(56) References Cited

U.S. PATENT DOCUMENTS 5,464,588 A * 11/1995 Bather ................. G01N 21/251
                                                    422/416
8,231,839 B2 * 7/2012 Robins ................ G01N 31/223
                                                    422/401
(Continued)

FOREIGN PATENT DOCUMENTS

CN          108681846 A       10/2018

*Primary Examiner* — Nader Bolourchi
(74) *Attorney, Agent, or Firm* — Muncy, Geissler, Olds & Lowe, P.C.

(57) ABSTRACT

The invention provides a system for managing food information based on an odor, which comprises a gas sensing module, a processing module, a blockchain module and a display module. The gas sensing module includes a colorimetric gas sensing chip reacting with odor molecules emitted by the food to form a coloring reaction and present a color image corresponding to the food. The processing module includes a conversion unit for converting the color image into identification information corresponding to the food. The blockchain module includes a plurality of nodes, and the plurality of nodes store identification information corresponding to the food. The display module includes an identification label corresponding to the identification information. Therefore, when the invention is applied to the blockchain technology, it can remove the doubt that the data on the chain can be falsified before the data is uploaded.

9 Claims, 4 Drawing Sheets

(51) Int. Cl.
  *G06K 9/62* (2006.01)
  *G06K 19/07* (2006.01)
  *G06Q 10/06* (2012.01)
  *G06Q 50/28* (2012.01)
  *H04L 9/06* (2006.01)

(52) U.S. Cl.
  CPC ............ *G06Q 10/06* (2013.01); *G06Q 50/28* (2013.01); *H04L 9/0643* (2013.01); *H04L 2209/38* (2013.01)

(58) Field of Classification Search
  CPC .. G06Q 10/0832; G06Q 10/087; G06Q 50/28; H04L 2209/38; H04L 9/0643; H04L 9/3239
  See application file for complete search history.

(56) References Cited

U.S. PATENT DOCUMENTS 10,295,473 B2 * 5/2019 Truex .................... G01N 21/783
2018/0284093 A1 * 10/2018 Brown .................... H04W 4/35

* cited by examiner

SYSTEM AND METHOD FOR MANAGING FOOD INFORMATION BASED ON ITS ODOR

FIELD OF THE INVENTION

The invention relates to a food information system, in particular to a system for managing food information applied to a blockchain technology.

BACKGROUND OF THE INVENTION

The appearance of the Internet breaks the space-time limitation of information transmission, and a huge amount of information can travel to and fro thousands of times between the two ends of the earth in the twinkling of an eye. Even after the advent of bitcoins, network technologies have revolutionized significantly, a most representative of which is a blockchain. After several years of development, the blockchain has many changes and extended applications, with practical cases in finance, medical treatment, property rights, identification, Internet of Things and many other fields currently. The reason why the blockchain is popular is that they are unforgeable and not easily modifiable. The decentralized blockchain technology enables all data on the chain to be public and transparent, people cannot tamper with the data anymore, or the data on the chain can be only changed at great cost.

In addition to the above-mentioned fields of application, practitioners applied blockchain technology on "food", which is the most human-related field, to maximize the functionality of blockchain technology. A related technology can refer to Chinese Patent Publication No. CN108681846A, which mentions a method and system for tracing food safety quality integrals, and the method comprises the steps of: acquiring various of detection data of agricultural products uploaded by each sensor detected in each production link, and determining quality integrals corresponding to the various detection data respectively based on a quality integral system; and establishing and storing a corresponding relationship between the agricultural products and the quality integral. In the case, it adopts the safety quality integral as a foundation accompanying with the blockchain technology as a means, which is used in the traceability mode of the food safety quality integral, to realize an operation mode of tracing and searching in the whole process among the growers, the manufacturers and the sales terminals, so as to achieve the traceability of agricultural product transaction.

However, the prior art still has problems to be improved, such as: how can we ensure the quality of food if all the data of blockchains is the fake data which is already altered before being uplinked?

Thus, techniques for verifying or ensuring correctness of the data on blockchains of the foods still have to be improved.

SUMMARY OF THE INVENTION

The main purpose of the present invention is to solve the problem that data of foods in blockchains may have been tampered before the data is uplinked.

To achieve the above object, the present invention provides a system for managing food information based on an odor, comprising a gas sensing module, a processing module, a blockchain module and a display module.

The gas sensing module includes at least one colorimetric gas sensing chip capable of reacting with at least one odor molecule emitted by the food to form at least one coloring reaction, wherein the colorimetric gas sensing chip includes a chemical reaction layer and a coloring reaction layer stacked with each other. The chemical reaction layer and the odor molecules generate a chemical reaction, and the coloring reaction layer generates the coloring reactions according to the chemical reaction to present at least one color image corresponding to the food.

The processing module includes a conversion unit for converting the color images into identification information corresponding to the food.

The blockchain module includes a plurality of nodes, wherein the plurality of nodes store the identification information corresponding to the food.

The display module includes an identification label corresponding to the identification information.

In an embodiment, the chemical reaction layer includes at least one reaction zone capable of reacting with the plurality of odor molecules to generate the chemical reaction, causing one side of the chemical reaction layer opposite to the coloring reaction layer to be served as an inlet side. The coloring reaction layer includes a coloring side and a reaction side, and the reaction side contacts the reaction zone of the chemical reaction layer, and the coloring reaction layer further includes a colorimetric indicator to generate the coloring reactions corresponding to the chemical reaction of the reaction side.

In an embodiment, the coloring side is further provided with a colorimetric block.

In an embodiment, the inlet side is further provided with at least one membrane layer selected from the group consisting of a water-resistant gas permeable membrane, an adsorbent layer, a diffusion membrane with a gas screening function, and a combination thereof.

In an embodiment, it further includes a communication module, wherein the communication module uploads the identification information to each of the plurality of nodes.

In an embodiment, the blockchain module further includes an intelligent contract trigger unit.

In an embodiment, the plurality of nodes further comprise a supply side, a logistics side, a demand side, or a combination thereof.

In an embodiment, the food is a fresh food.

In an embodiment, the identification label is further a one-dimensional bar code, a two-dimensional bar code, a pattern tag, a radio frequency identification system (RFID) electronic label, or a combination thereof.

The invention further provides a method for managing food information based on an odor, which comprises the steps of:

S1: providing a gas sensing module including at least one colorimetric gas sensing chip, and enabling the colorimetric gas sensing chip to react with at least one odor molecule emitted by a food to form at least one coloring reaction, wherein the colorimetric gas sensing chips are respectively stacked with a chemical reaction layer and a coloring reaction layer;

S2: enabling the chemical reaction layer and the odor molecules to generate a chemical reaction, enabling the coloring reaction layer to generate the coloring reactions according to the chemical reaction to present at least one color image corresponding to the food, and converting the color images into identification information corresponding to the food by a conversion unit of a processing module;

S3: providing a communication module to upload the identification information to a blockchain module includes a plurality of nodes, and enabling the plurality of nodes to store the identification information corresponding to the food; and S4: enabling a display module to form an identification label corresponding to the identification information.

Accordingly, due to the fact that the colorimetric gas sensing chip outputs the information which is real-time and unforgeable, the doubt that the data on the chain can be falsified before being uploaded is removed by using the blockchain technology, and the user can access the blockchain via the network at any time and any place to confirm whether the information on the chain is abnormal or whether the food is true or false by the setting of the identification label. In short, the invention provides a method for a person having ordinary skill in the art to ensure that all data on a food information blockchain are correct, which greatly improves the authenticity and the possibility of tempering the data on the blockchain, and even reduces food security crisis.

DETAILED DESCRIPTION OF THE PREFERRED EMBODIMENTS

With regard to the detailed description and technical aspects of the present invention is described with reference to the accompanying drawings as follows.

Figure 1:
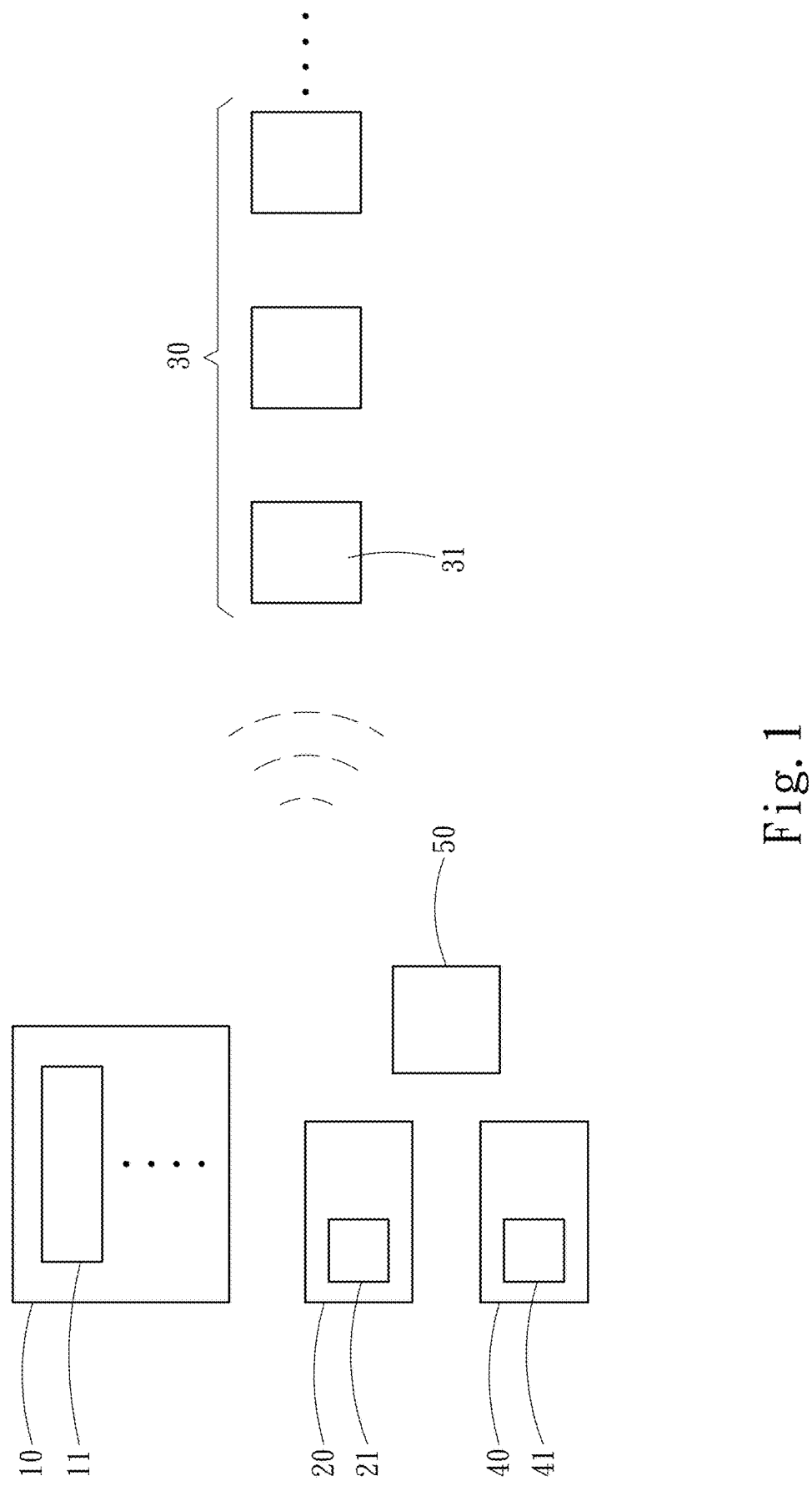
FIG. 1 is a schematic diagram showing the structure of a system according to an embodiment of the present invention.

With reference to FIG. 1, the invention provides a system for managing food information based on an odor, which comprises a gas sensing module 10, a processing module 20, a blockchain module 30, and a display module 40.

Figure 2:
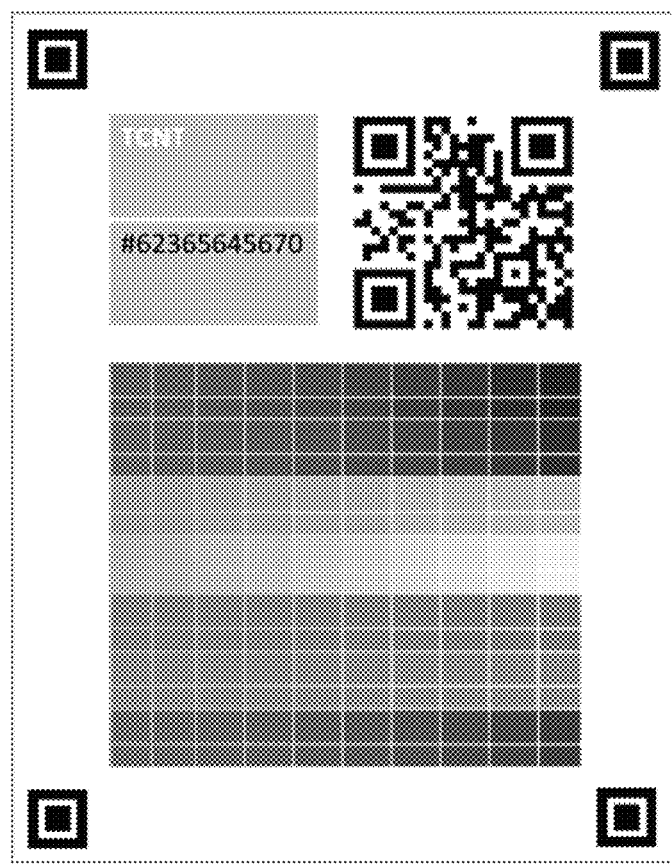
FIG. 2 is a schematic view showing the appearance of a colorimetric gas sensing chip according to an embodiment of the present invention.
Figure 3:
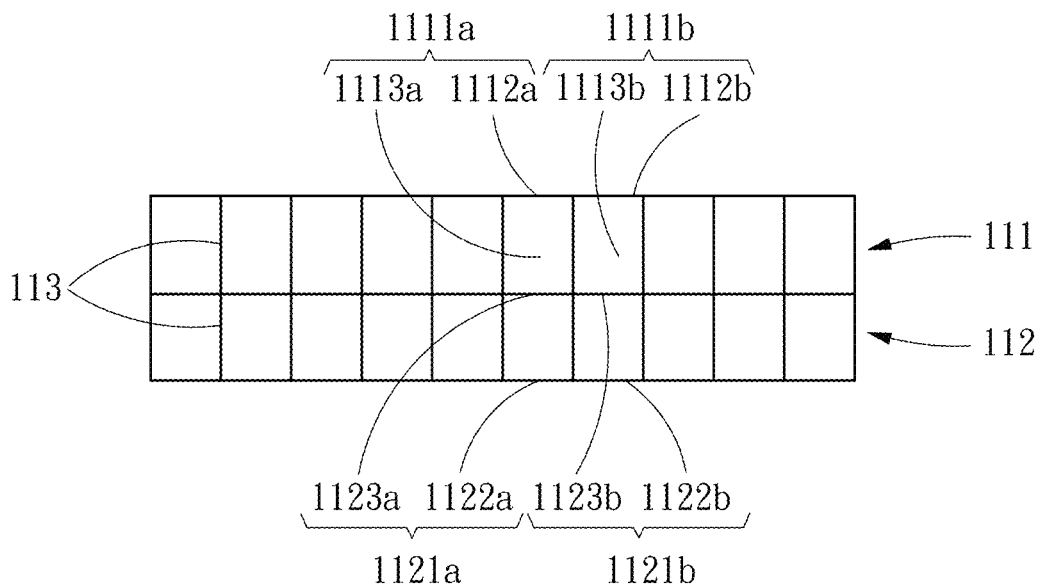
FIG. 3 is a schematic diagram showing the structure of the colorimetric gas sensing chip according to an embodiment of the present invention.
Figure 4:
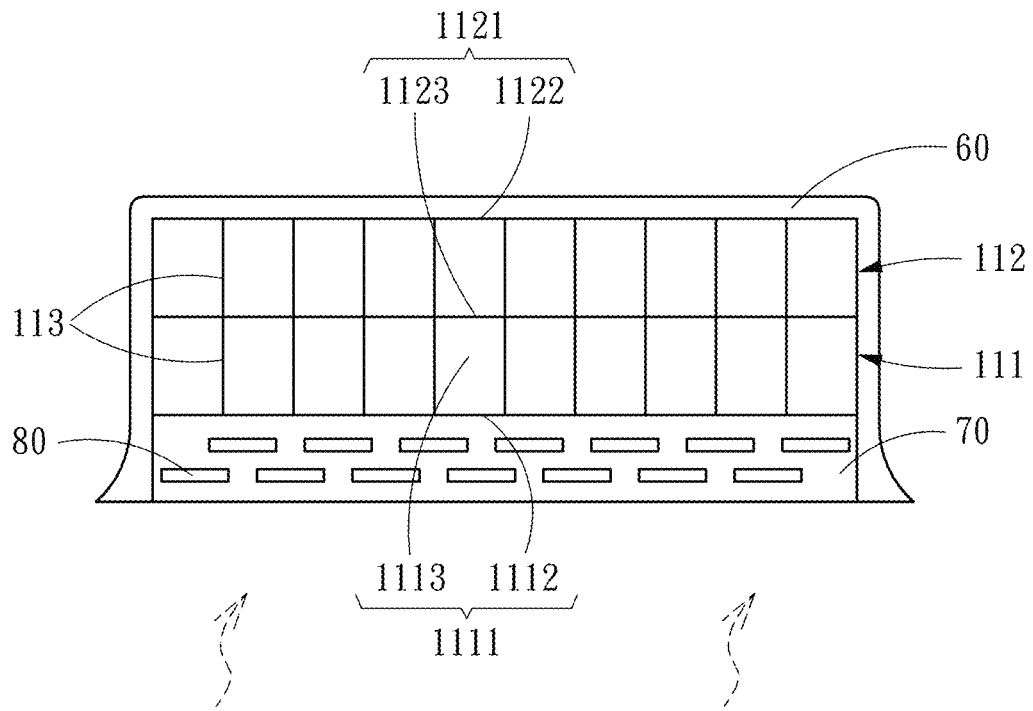
FIG. 4 is a schematic diagram showing the structure of the colorimetric gas sensing chip according to another embodiment of the present invention.

With reference to FIG. 1 and FIG. 2, the gas sensing module 10 includes at least one colorimetric gas sensing chip 11, that is, the gas sensing module 10 is provided with one or more colorimetric gas sensing chips 11, and the present invention is not limited thereto. In an embodiment, the gas sensing module 10 is a test paper, but is not limited thereto. The colorimetric gas sensing chip 11 reacts with at least one odor molecule emitted by a food to form at least one coloring reaction. As shown in FIGS. 3 and 4, the colorimetric gas sensing chip 11 includes a chemical reaction layer 111 and a coloring reaction layer 112 stacked with each other. In detail, the chemical reaction layer 111 generates a chemical reaction with the odor molecules, and the coloring reaction layer 112 generates the coloring reactions according to the chemical reaction to present at least one color image corresponding to the food. Briefly, the colorimetric gas sensing chip 11 chemically reacts with the odor molecules emitted by the food so that the gas sensing module 10 forms the color images corresponding to the food.

The source of the food is a raw and fresh food, or a take-away meal. More specifically, any food capable of emitting odors such as vegetable, fruit, meat, bento, and the like can be used in the present invention, but is not limited thereto.

In addition to the colorimetric gas sensing chip 11 including the chemical reaction layer 111 and the coloring reaction layer 112 stacked with each other, the colorimetric gas sensing chip 11 further includes a partition portion 113, which will be described in detail below.

With reference to FIGS. 3 and 4, the chemical reaction layer 111 is divided into a plurality of first areas 1111 by the partition portion 113. Each of the plurality of first areas 1111 includes an inlet side 1112 on one side opposite to the coloring reaction layer 112 and a reaction zone 1113. The odor molecules enter the reaction zone 1113 from the inlet side 1112, and each of the reaction zones 1113 reacts with the odor molecules to generate the chemical reaction. Each of the reaction zones 1113 includes different types of chemicals to react with different target gases. For example, some reaction zones 1113 react with alkanes; some reaction zones 1113 react with alcohols; and some reaction zones 1113 react with sulfides, etc. The partition portion 113 separates adjacent first areas 1111 so that the adjacent first areas 1111 do not affect each other. The chemical reaction is a redox reaction, an acid-base reaction, a ferment catalytic reaction, a metal catalytic reaction, a condensation reaction, a hydrolysis reaction, an addition reaction, an elimination reaction, a substitution reaction, or a combination thereof, but is not limited thereto. For example, one suitable redox reaction suitable for the invention is oxidation of ethanol to acetaldehyde or acetic acid; and a glucose oxidase is used in an enzyme-catalytic reaction; and a platinum catalyst is used in a metal-catalysis reaction. Alternatively, assuming that one of the reaction zones 1113 is coated with hydrazine ($H_2N-NH_2$), carbazic acid ($H_2NNHCOOH$) is generated when the odor molecules including carbon dioxide react with the reaction zone 1113 coated with hydrazine, and a color is generated by using a Crystal violet as a redox indicator. Also, in an embodiment, the colorimetric gas sensing chip 11 further includes a protective layer provided on the inlet side 1112 to prevent interference or damage caused by the gas directly entering the reaction zones 1113.

The coloring reaction layer 112 is also separated by a partition portion 113 to include a plurality of second areas 1121, the second areas 1121 and the first areas 1111 are correspondingly stacked with each other, and each of the second areas 1121 includes a coloring side 1122, and a reaction side 1123 in contact with the reaction area 1113 of the chemical reaction layer 111. The coloring reaction layer 112 includes a coloring indicator, so that when the reaction zone 1113 generates the chemical reaction, the coloring reaction layer 112 in contact with the reaction zone 1113 generates the coloring reaction corresponding to the chemical reaction.

The composition of the coloring indicator is selected from the group consisting of a hydrate, a precipitate, a metal coordination compound, and a combination thereof. Take the hydrate as an example, it can be dry cobaltous chloride which becomes pink hydrate when meets water vapor; take the precipitate as an example, it can be black lead sulfide precipitate produced when lead acetate meets hydrogen sulfide; and take the metal coordination compound for an example, it can be oxygen coordinating and combining with iron ions in heme to present bright red color. Further, the "coloring indicator" suitable for use in the present invention is not particularly limited. For example, the coloring indicator is an acid-base indicator, a solvatochromism, or a combination thereof. For instance, the acid-base indicator is a colorimetric reagent such as Bromohymol Blue, phenolphthalein, and the like.

In this embodiment, each of the first areas 1111 is further divided into the first areas 1111a, 1111b, each of the second areas 1121 is further divided into the second areas 1121a, 1121b, the inlet side 1112 is divided into the inlet sides 1112a, 1112b, and the reaction zone 1113 is divided into the reaction zones 1113a, 1113b. The second area 1121 is further divided into the second areas 1121a, 1121b, the coloring side 1122 is divided into the coloring sides 1122a, 1122b, and the reaction side 1123 is divided into the reaction sides 1123a, 1123b. The partition portion 113 is a partition wall separating the adjacent first areas 1111a, 1111b and the adjacent second areas 1121a, 1121b, so that the odor molecules enter the inlet side 1112a and react with the reaction zone 1113a without affecting the adjacent reaction zone 1113b, and the reaction in the reaction zone 1113a only affects the reaction side 1123a and the coloring side 1122a, without affecting the reaction side 1123b and the coloring side 1122b.

In an embodiment, an anti-reflection film 60 is further disposed at an outermost side of the colorimetric gas sensing chip 11, which helps a user to observe the color change of the coloring side 1122 through an instrument or the naked eyes from the outside without interference. At least one layer of diffusion membranes 70 including an odor molecule screening function are provided to achieve the effect of screening specific odor molecules. The diffusion membrane 70 is disposed outside the chemical reaction layer 111, in more detail, the outside the chemical reaction layer 111 is near the inlet side 1112.

In an embodiment that a plurality of diffusion membranes 70 are provided, each diffusion membrane 70 is designed to block the different odor molecules. In addition, in an embodiment, a graphene 80 with various sizes is added to each diffusion membrane 70 to adjust the diffusion paths of the odor molecules in the plurality of diffusion membranes 70, and thus the diffusion speed of the molecules is changed to obtain the effect of screening macromolecules or macromolecules.

To more efficiently adsorb the odor molecules, the present invention further includes an adsorption molecule in the diffusion membrane 70 to achieve the above object. The adsorption molecule is any liquid, colloids, pores, or fibrous membranes including an adsorbent function. In an embodiment, glycerol is used as the adsorption molecule. However, it is also possible to directly dispose an adsorbent layer including adsorption molecules between a pair of diffusion membranes 70, which can also obtain a good adsorption effect.

In addition, in the various embodiments described in the foregoing, a water-resistant gas permeable membrane is selectively provided at an appropriate position near the inlet side 1112 of the chemical reaction layer 111, to reduce the interference of the external environment to the internal chemical reaction. In general, the membrane layer is selected from the group consisting of the breathable membrane, the adsorbent layer, the diffusion membrane 70, and a combination thereof.

According to the invention, a plurality of colorimetric blocks can be arranged, so that the colorimetric blocks are corresponding arranged with the reaction zones 1113, and thereby the color identification is easier, and then the identification error is reduced.

In the above embodiments, the order of the chemical reaction layer 111, the coloring reaction layer 112, or other functional layers may be exchanged with one another without limitation, on the premise that the plurality of odor molecules may enter the chemical reaction layer 111 and react with the plurality of reaction zones 1113.

From the above description, the colorimetric gas sensing chip 11 in the gas sensing module 10 of the present invention has been described in series, and the next will be the processing module 20. The processing module 20 includes a conversion unit 21 for converting the color images into identification information corresponding to the food. That is, the color images are converted into the identification information corresponding to the food by the processing module 20. The conversion unit 21 acquires a color information of the color images by, for example, the instrument (not shown in FIGS.), and then the conversion unit 21 converts the color information obtained into the identification information corresponding to the food. Image acquiring and identifying color is common techniques in an image processing field, and details thereof are omitted here for brevity. The identification information is data information or anything representing the identification of the at least one odor molecule emitted by the food, but is not limited thereto. In an embodiment, the processing module 20 is a remote server or a handheld electronic device, but is not limited thereto.

In addition, the gas sensing module 10 is not limited to be only one colorimetric gas sensing chip 11 but more than one colorimetric gas sensing chip 11 can be provided according to practical requirements. That is, it can be applied to various food and form different color images or even identification information, which would not be further elaborated in this paragraph since it can be easily understood and is included in the following description.

Furthermore, the blockchain module 30 includes a plurality of nodes 31, and the plurality of nodes 31 store the identification information corresponding to the food. Also, the plurality of nodes 31 is not limited to record only one identification information but store more than one identification information according to practical requirements, and the food corresponding to the identification information is different from each other. For instance, the plurality of nodes 31 are a supply side, a logistics side, a demand side, or a combination thereof. More specifically, the nodes 31 are a food manufacturer, a freight logistics provider, a retail manufacturer, etc, but it is not limited thereto. In an embodiment, the blockchain module 30 further has an intelligent contract trigger unit to enhance the use function of the blockchain module 30.

In an embodiment, the present invention further includes a communication module 50, and the communication module 50 uploads the identification information to each of the nodes 31. Additionally, the plurality of nodes 31 of the blockchain module 30 are pre-stored with the identification information corresponding to the food. Therefore, newer or corrected identification information is then uploaded to each of the plurality of nodes 31 via the communication module 50. In an embodiment, the communication module 50 is a handheld electronic device, but is not limited thereto.

Regarding the display module 40, an identification label 41 corresponding to the identification information is provided. Specifically, the identification label 41 is a one-dimensional barcode, a two-dimensional barcode, a pattern tag, a radio frequency identification system (RFID) electronic label, or a combination thereof, but is not limited thereto. That is, the present invention converts the color images into the identification label 41 corresponding to the color images. Then, the user can check the correctness of the identification information on the plurality of nodes 31 of the blockchain module 30 or the authenticity of the food source at any time by connecting the identification label 41 to the blockchain network. In an embodiment, the display module 40 is a screen of a handheld electronic device, but is not limited thereto.

Figure 5:
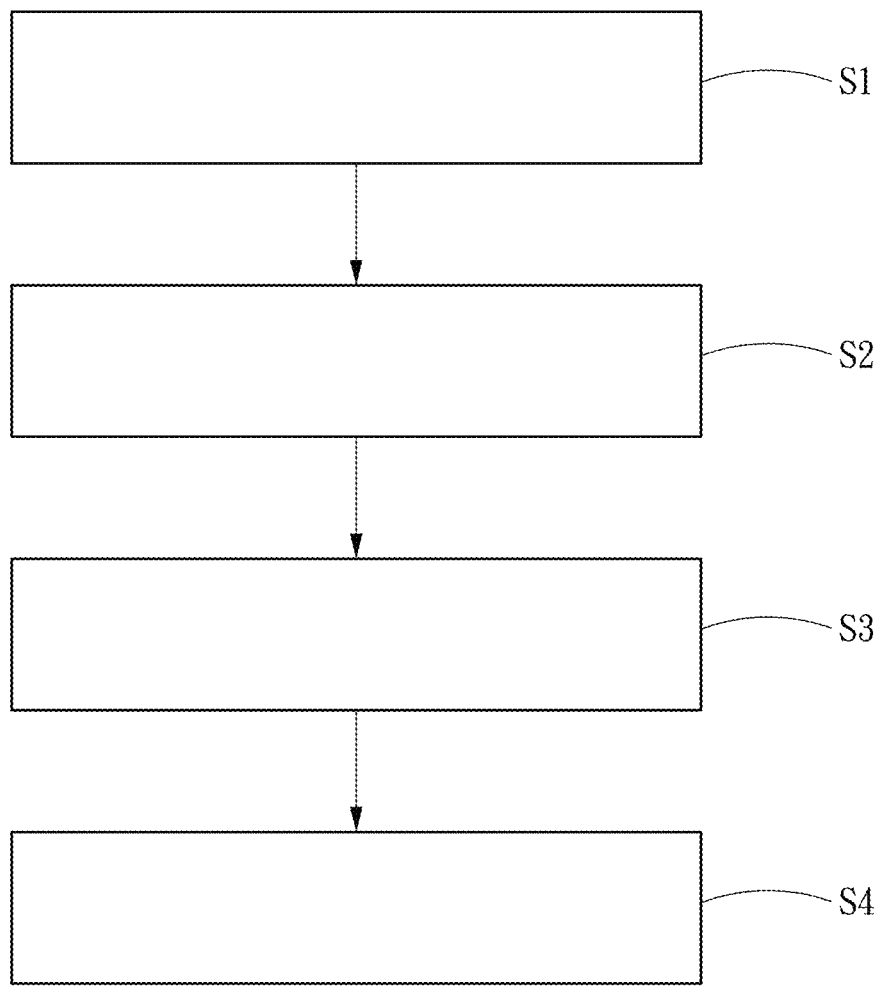
FIG. 5 is a flow chart showing an operation method according to an embodiment of the present invention.

Further, an operation method of the present invention is described with reference to FIG. 5:

S1: providing the gas sensing module 10, and causing the colorimetric gas sensing chip 11 to react with the odor molecules emitted by the food to form the coloring reactions;

S2: enabling the chemical reaction layer 111 and the odor molecules generate the chemical reaction, and the coloring reaction layer 112 generating the coloring reactions according to the chemical reaction to present the color images corresponding to the food, and converting the color images into the identification information corresponding to the food by the conversion unit 21 of the processing module 20;

S3: providing a communication module 50 to upload the identification information to the blockchain module 30, and enabling the plurality of nodes 31 to store the identification information corresponding to the food; and S4: causing the display module 40 to form the identification label 41 corresponding to the identification information.

Accordingly, due to the fact that the colorimetric gas sensing chip outputs the information which is real-time and unforgeable, the doubt that the data on the chain is falsified before being uploaded is removed by using the blockchain technology, and the user can access the blockchain via the network at any time and any place to confirm whether the information on the chain is abnormal or whether the food is true or false by the setting of the identification label. In short, the invention provides a method to ensure that all data on a food information blockchain are correct, which greatly improves the authenticity and unforgeability of the data on the blockchain, and even reduces food security crisis.

What is claimed is:

1. A system for managing food information based on an odor, comprising:
    a gas sensing module including at least one colorimetric gas sensing chip reacting with at least one odor molecule emitted by a food to form at least one coloring reaction, wherein the at least one colorimetric gas sensing chip comprises a chemical reaction layer and a coloring reaction layer stacked with each other, the chemical reaction layer and the at least one odor molecule generates a chemical reaction, and the coloring reaction layer generates the at least one coloring reaction according to the chemical reaction to present at least one color image corresponding to the food;
    a processing module, including a conversion unit for converting the at least one color image into identification information corresponding to the food;
    a blockchain module, including a plurality of nodes, wherein the plurality of nodes store the identification information corresponding to the food; and
    a display module, including an identification label corresponding to the identification information.

2. The system as claimed in claim 1, wherein the chemical reaction layer includes at least one reaction zone reacting with the at least one odor molecule to generate the chemical reaction, and one side of the chemical reaction layer opposite to the coloring reaction layer serves as an inlet side, and the coloring reaction layer includes a coloring side and a reaction side which are correspondingly disposed, the reaction side is in contact with the at least one reaction zone of the chemical reaction layer, and the coloring reaction layer further includes a coloring indicator to generate the at least one coloring reaction corresponding to the chemical reaction of the reaction side.

3. The system as claimed in claim 2, wherein the coloring side is further provided with a colorimetric block.

4. The system as claimed in claim 2, wherein the inlet side is further provided with at least one membrane layer selected from a group consisting of a water-resistant gas permeable membrane, an adsorbent layer, a diffusion membrane with a gas screening function, and a combination thereof.

5. The system as claimed in claim 1, wherein the system further comprises a communication module, and the communication module uploads the identification information to each of the plurality of nodes.

6. The system as claimed in claim 1, wherein the plurality of nodes further comprise a supply side, a logistics side, a demand side, or a combination thereof.

7. The system as claimed in claim 1, wherein the food is a fresh food.

8. The system as claimed in claim 1, wherein the identification label is further a one-dimensional bar code, a two-dimensional bar code, a pattern tag, a radio frequency identification system (RFID) electronic label, or a combination thereof.

9. A method for managing food information based on an odor, comprising the steps of:
    S1: providing a gas sensing module including at least one colorimetric gas sensing chip, and enabling the at least one colorimetric gas sensing chip to react with at least one odor molecule emitted by a food to form at least one coloring reaction, wherein the at least one colorimetric gas sensing chip is stacked with a chemical reaction layer and a coloring reaction layer;
    S2: enabling the chemical reaction layer and the at least one odor molecule to generate a chemical reaction, enabling the coloring reaction layer to generate the at least one coloring reaction according to the chemical reaction to present at least one color image corresponding to the food, and converting the at least one color image into identification information corresponding to the food by a conversion unit of a processing module;
    S3: providing a communication module to upload the identification information to a blockchain module including a plurality of nodes, and enabling the plurality of nodes to store the identification information corresponding to the food; and
    S4: enabling a display module to form an identification label corresponding to the identification information.

* * * * *